US009782299B2

(12) United States Patent
Croizat et al.

(10) Patent No.: US 9,782,299 B2
(45) Date of Patent: Oct. 10, 2017

(54) ABDOMINAL WOUND DRESSING COMPRISING JOINING MEANS

(71) Applicant: Paul Hartmann AG, Heidenheim (DE)

(72) Inventors: Pierre Croizat, Herbrechtingen (DE); Axel Eckstein, Heidenheim (DE); Cornelia Wolf, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 512 days.

(21) Appl. No.: 14/176,685

(22) Filed: Feb. 10, 2014

(65) Prior Publication Data
US 2014/0228787 A1    Aug. 14, 2014

Related U.S. Application Data

(60) Provisional application No. 61/765,189, filed on Feb. 15, 2013.

(30) Foreign Application Priority Data

Feb. 13, 2013  (DE) ........................ 10 2013 002 521

(51) Int. Cl.
*A61F 13/00* (2006.01)
*A61M 1/00* (2006.01)

(52) U.S. Cl.
CPC .. *A61F 13/00029* (2013.01); *A61F 13/00068* (2013.01); *A61M 1/0088* (2013.01)

(58) Field of Classification Search
CPC combination set(s) only.
See application file for complete search history.

(56) References Cited

U.S. PATENT DOCUMENTS 7,279,612 B1 * 10/2007 Heaton ............. A61F 13/00021
602/3
7,951,100 B2 * 5/2011 Hunt .................... A61M 1/0088
602/2
(Continued)

FOREIGN PATENT DOCUMENTS

DE  102010052336 A1   5/2012
DE  102013002521 A1   8/2014
(Continued)

OTHER PUBLICATIONS

International Preliminary Report on Patentability and Written Opinion dated Aug. 27, 2015 for International Application No. PCT/EP2014/052748.

*Primary Examiner* — Todd J Scherbel
*Assistant Examiner* — Guy K Townsend
(74) *Attorney, Agent, or Firm* — Dilworth & Barrese, LLP

(57) ABSTRACT

The invention relates to an apparatus suitable for use in the negative-pressure therapy of the open abdomen, including a first bandage ply (11, 21, 31) having a first and a second side, as organ-protecting layer, the first side being intended for application to a wound base (3), more particularly exposed internal organs or the greater omentum, a second bandage ply (12, 22) provided separately from the first bandage ply and having a first and a second side, the first side of the second bandage ply (12, 22) being intended for application to the second side of the first bandage ply, a joining means by means of which the second bandage ply (12, 22), after application of the first ply (11, 21, 31) to exposed internal organs or to the greater omentum, can be joined to the first bandage ply (11, 21, 31), making it possible to avoid movement of the first bandage ply (11, 21, 31) with respect to the second bandage ply (12, 22) as far as possible during (Continued)

the therapy and/or facilitating simultaneous removal of first (11, 21, 31) and second bandage ply (12, 22).

10 Claims, 3 Drawing Sheets

(56) References Cited

U.S. PATENT DOCUMENTS

| | | | | |
|---|---|---|---|---|
| 8,114,126 | B2* | 2/2012 | Heaton | A61M 1/0088 602/42 |
| 8,142,419 | B2* | 3/2012 | Heaton | A61M 1/0088 604/289 |
| 8,192,409 | B2* | 6/2012 | Hardman | A61M 1/0088 604/327 |
| 8,257,327 | B2* | 9/2012 | Blott | A61M 1/0058 604/313 |
| 8,469,935 | B2* | 6/2013 | Simmons | A61M 1/0088 604/313 |
| 8,535,296 | B2* | 9/2013 | Blott | A61M 1/0058 604/304 |
| 8,551,075 | B2* | 10/2013 | Bengtson | A61M 1/008 604/541 |
| 8,603,053 | B2 | 12/2013 | Riesinger | |
| 2007/0141128 | A1* | 6/2007 | Blott | A61M 1/0058 424/445 |
| 2008/0243044 | A1* | 10/2008 | Hunt | A61M 1/0088 602/58 |
| 2009/0099519 | A1* | 4/2009 | Kaplan | A61F 7/12 604/113 |
| 2009/0318842 | A1* | 12/2009 | Kairinos | A61F 13/0216 602/52 |
| 2010/0106115 | A1* | 4/2010 | Hardman | A61M 1/0088 604/319 |
| 2010/0106188 | A1* | 4/2010 | Heaton | A61M 1/0088 606/216 |
| 2011/0112492 | A1* | 5/2011 | Bharti | A61M 1/0088 604/319 |
| 2011/0152800 | A1* | 6/2011 | Eckstein | A61F 13/0216 604/319 |
| 2011/0224630 | A1* | 9/2011 | Simmons | A61F 13/00068 604/317 |
| 2011/0251567 | A1* | 10/2011 | Blott | A61M 1/0001 604/290 |
| 2011/0270301 | A1* | 11/2011 | Cornet | A61B 17/085 606/213 |
| 2012/0136326 | A1* | 5/2012 | Croizat | A61F 13/00017 604/319 |
| 2014/0228787 | A1* | 8/2014 | Croizat | A61F 13/00029 604/319 |
| 2014/0228788 | A1 | 8/2014 | Croizat et al. | |

FOREIGN PATENT DOCUMENTS

| | | |
|---|---|---|
| WO | 01/85248 A1 | 11/2001 |
| WO | 2013/012381 A1 | 1/2013 |
| WO | 2013/034262 A1 | 3/2013 |
| WO | 2013/034263 A1 | 3/2013 |

* cited by examiner

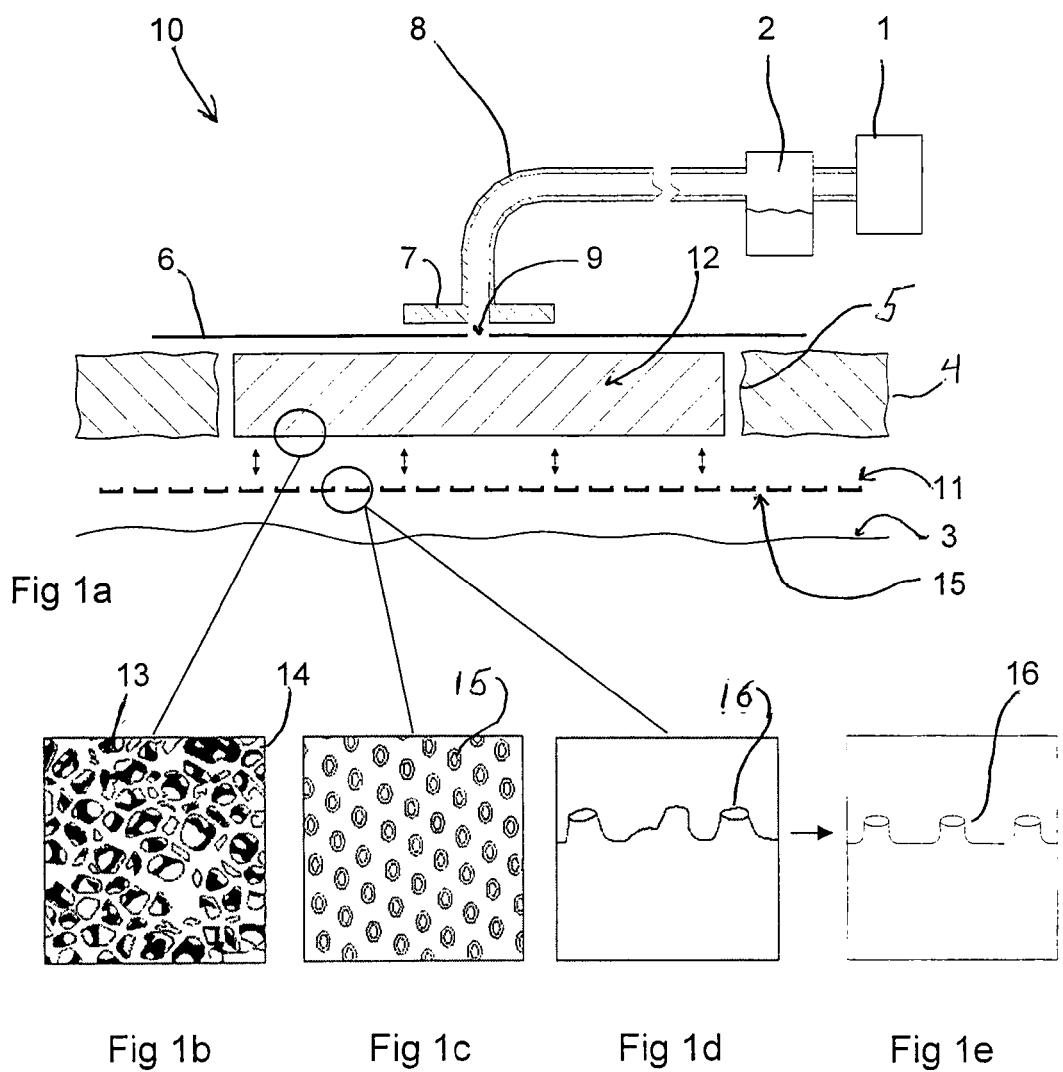

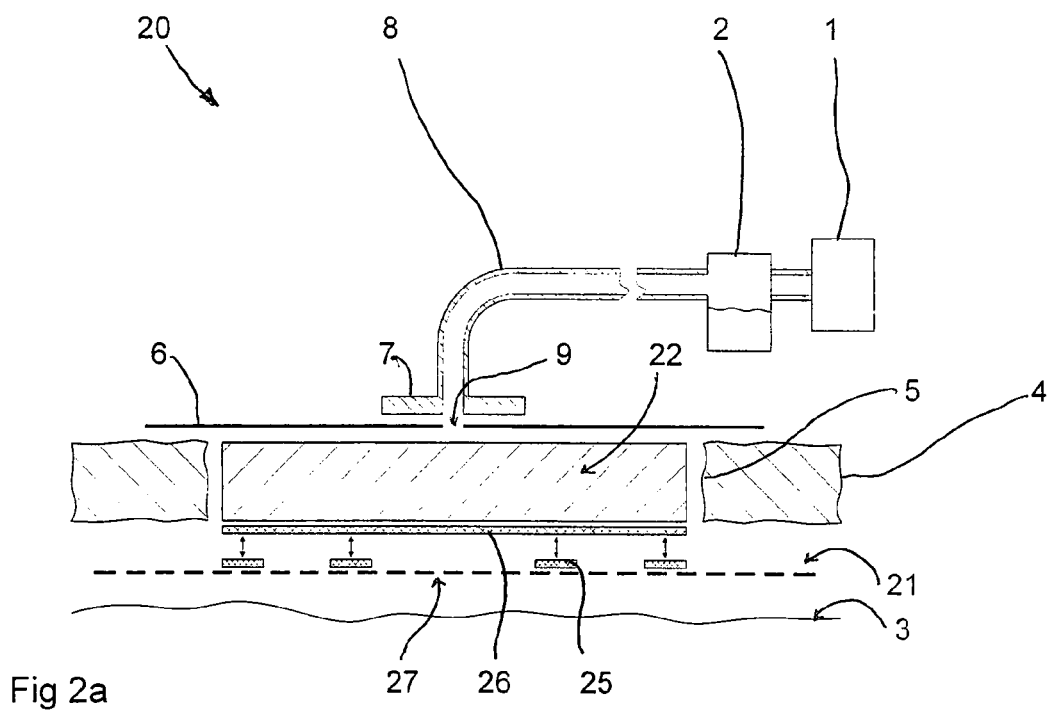
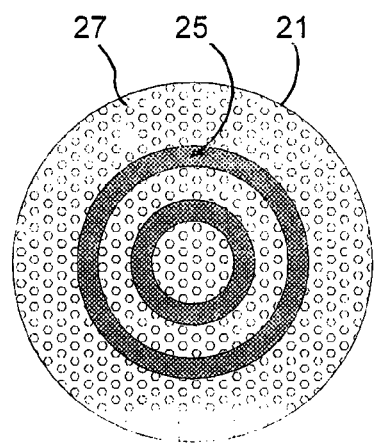
Fig 2b
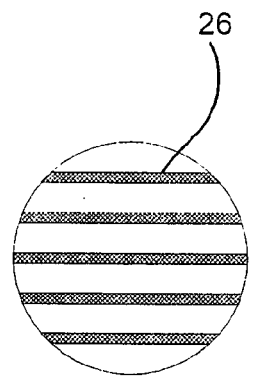
Fig 2c

ABDOMINAL WOUND DRESSING COMPRISING JOINING MEANS

CROSS-REFERENCE TO RELATED APPLICATIONS

The present application claims priority to U.S. Provisional Application No. 61/765,189 filed Feb. 15, 2013, and to German Application No. DE 10 2013 002 521.4 filed Feb. 13, 2013, both of which are incorporated by reference herein.

DESCRIPTION

The present invention relates to an apparatus for use in the negative-pressure therapy of wounds, more particularly wounds in the abdominal region, comprising a first bandage ply having a first and a second side, as organ-protecting layer, the first side being intended for application to exposed internal organs or to the greater omentum, a second bandage ply provided separately from the first bandage ply and having a first and a second side, the first side of the second bandage ply being intended for application to the second side of the first bandage ply, and a joining means by means of which the second bandage ply, after application of the first ply to exposed internal organs or to the greater omentum, can be joined to the first bandage ply, making it possible to avoid movement of the first bandage ply with respect to the second bandage ply as far as possible during the therapy and/or facilitating simultaneous removal of first and second bandage ply.

Apparatuses for the negative-pressure therapy of wounds and bandages as part of such apparatuses are known in the prior art. For example, WO1993/009727 describes an apparatus for promoting wound healing through the application of negative pressure to the skin region comprising the wound and surrounding the wound.

During the negative-pressure therapy of wounds, a negative-pressure-generating device communicates via a suction line with the wound or the wound space, where an airtight and negative-pressure-tight wound bandage is provided for airtight and negative-pressure-tight closure of the wound and the wound space, making it possible to establish negative pressure in the wound space and to aspirate fluids from the wound space into a container typically arranged between the negative-pressure-generating device and the wound.

In this connection, the expression "negative pressure" refers to air pressure which is reduced within the wound bandage with respect to the ambient air pressure (atmospheric air pressure). "Within the wound bandage" is understood to mean the gap (wound space) formed by the airtight covering material and the body tissue in the wound region. "Negative pressure" is frequently also referred to as "reduced pressure". In the context of the invention, the pressure difference between the air pressure within the wound bandage and the ambient air pressure is specified in mmHg (millimeters of mercury), since this is conventional in the field of negative-pressure therapy. 1 mmHg corresponds to one Torr or 133.322 Pa (pascal). In the context of the invention, the negative pressure, i.e. the pressure difference between the air pressure within the wound bandage and the ambient air pressure, is specified as a positive numerical value in mmHg.

Wounds which are particularly large in area can arise in the abdominal region either as a result of injuries or as a result of surgical interventions. Surgical interventions in the abdominal region are, for example, undertaken in the case of operative treatment of acute and life-threatening diseases of the abdominal cavity. As part of the postoperative care of such surgical interventions, there may also be the need to only temporarily cover the open abdominal region using a temporary wound closure. During the treatment of a wound on the open abdomen, it may be necessary to drain a very large amount of fluid, for example up to 5 l within 48 hours. Very large amounts of fluid to be drained may, for example, arise during the operative treatment of nonmechanical intestinal obstruction (ileus) or of inflammation of the peritoneum (peritonitis). In the case of an abdominal wound, exposed internal organs or the greater omentum (also referred to as epiploon) form a wound base, i.e. a body surface situated within a wound edge. During the care of an abdominal wound, a fluid-permeable material ply (hereinafter also referred to as organ-protecting layer) is normally directly applied to exposed internal organs or to the greater omentum. During the negative-pressure treatment of an abdominal wound, the fluid-permeable wound contact layer lying on the exposed internal organs or the greater omentum also serves as an organ-protecting layer which is intended to prevent undesired adhesive bonding of organs or the greater omentum to the abdominal wall and/or undesired adhesive bonding of organs or the greater omentum to a further bandage ply, for example a wound dressing composed of a foam. The edge region of the wound dressing is usually introduced into the gap formed by abdominal wall and internal organs. At least one further fluid-permeable layer is typically applied to the side of the organ-protecting layer that is facing away from the wound during use. The further ply is frequently a porous polymer foam, more particularly one composed of polyurethane. Such a bandage for the temporary covering of wounds resulting from accidents or surgical interventions, more particularly abdominal wounds (hereinafter also referred to as "abdominal bandage"), is, for example, known from WO01/85248. The bandage is intended for use in negative-pressure therapy. WO01/85248 proposes covering the wound base with a film having holes. A porous foam is applied to the film constituting the wound contact layer. On the side facing away from the wound, the bandage comprises a fluid-impermeable covering film having an adhesive edge for airtight closure of the wound region. In addition, connecting means are provided which extend through the covering film up to the porous foam in order to be able to connect the wound space to a negative-pressure source. During operation, wound exudate can be removed from the wound space, by the fluid reaching firstly the porous foam through the openings of the perforated film and, further on, the connecting means via the foam, which connecting means is in direct contact with the porous foam.

Patent application DE102010052336 from the applicant of the present patent application likewise describes a bandage for use in the negative-pressure therapy of wounds, more particularly wounds in the abdominal region, comprising a flexible perforated film as organ-protecting layer and at least one conducting means applied to the film. The bandage can comprise one or more fluid-permeable layers, for example layers composed of a polymer foam.

In practice, it has been found that, in the case of the negative-pressure therapy of the open abdomen using abdominal bandages comprising at least two layers composed of different material plies, the individual material plies may be undesirably moved with respect to one another during the treatment. More particularly, it was observed that an organ-protecting layer initially uniformly applied to exposed internal organs or to the greater omentum may slip out of place during the negative-pressure treatment. Movement of the individual material plies with respect to one another or the organ-protecting layer slipping out of place may lead to undesired complications which may endanger the outcome of treatment with the negative-pressure therapy. More particularly, when the organ-protecting layer moves with respect to the further material ply during the treatment, the further material ply may come into direct contact with the exposed internal organs or with the greater omentum, and so adhesive bonding between body tissue and the further material ply may occur. When detaching the further material ply, for example a foam, from the wound base during bandage change, damage to the exposed tissues may occur. Damage to the exposed tissues may lead, inter alia, to fistula formation. In addition, it is undesirable for the edge region of the organ-protecting layer, which is usually introduced into the gap formed by abdominal wall and internal organs to prevent undesired adhesive bonding of organs or the greater omentum to the abdominal wall, to be pulled out of the gap during the treatment.

It is therefore particularly an object of the present invention to reliably avoid such complications which occur during the negative-pressure therapy of the open abdomen. Here, the intention of the present invention is to contribute in general to further improving the negative-pressure therapy of the open abdomen, which therapy is usually associated with serious and life-threatening medical conditions, and to facilitating use, especially during bandage change.

To this end, the invention proposes an apparatus suitable for use in the negative-pressure therapy of the open abdomen, comprising a first bandage ply having a first and a second side, as organ-protecting layer, the first side being intended for application to a wound base, more particularly exposed internal organs or the greater omentum, a second bandage ply provided separately from the first bandage ply and having a first and a second side, the first side of the second bandage ply being intended for application to the second side of the first bandage ply, and a joining means by means of which the second bandage ply, after application of the first ply to the wound base, more particularly exposed internal organs or the greater omentum, can be joined to the first bandage ply. Here, it is essential to the invention that the joining means is suitable for avoiding movement of the first bandage ply with respect to the second bandage ply as far as possible during the therapy and/or facilitating simultaneous removal of first and second bandage ply.

In a further aspect of the invention, a first product for use in the therapeutic treatment of the open abdomen on the human or animal body by means of negative pressure is proposed. Here, the first product is thus expressly claimed in connection with its specific medical use or indication, viz. the negative-pressure treatment of the open abdomen. The first product comprises a first bandage ply having a first and a second side, as organ-protecting layer, the first side being intended for application to a wound base, more particularly exposed internal organs or the greater omentum, a second bandage ply provided separately from the first bandage ply and having a first and a second side, the first side of the second bandage ply being intended for application to the second side of the first bandage ply, and a joining means by means of which the second bandage ply, after application of the first ply to the wound base, more particularly exposed internal organs or the greater omentum, can be joined to the first bandage ply, it being possible for the first bandage ply, during the therapy, to be held in the abdominal space at the position desired by the user by means of the second bandage ply and/or it being possible to safely remove the first bandage ply from the abdominal space after completion of the negative-pressure therapy by taking out the second bandage ply.

The invention likewise relates to a second product for use in the therapeutic treatment of the open abdomen on the human or animal body by means of negative pressure. The second product comprises an organ-protecting layer. Here, the second product is expressly claimed in connection with its specific medical use, viz. use as organ-protecting layer in the therapeutic treatment of the open abdomen on the human or animal body by means of negative pressure. The organ-protecting layer has a first and a second side, the first side being intended for application to a wound base, more particularly exposed internal organs or the greater omentum. The second side comprises a joining means, making it possible, after laying the organ-protecting layer on the wound base, more particularly exposed internal organs or the greater omentum, to establish a connection with a further bandage ply. Preferably, the organ-protecting layer comprises a fluid-permeable textile material or a fluid-permeable flexible film composed of a polymeric material. More particularly, the organ-protecting layer comprises a flexible perforated film, wherein the perforations are introduced into the film such that the perforation edges protrude from the second surface of the film, and so three-dimensional structures, more particularly crater-shaped structures, are present on the second surface of the film.

The invention therefore also provides an organ-protecting layer for use in the therapeutic treatment of the open abdomen on the human or animal body by means of negative pressure, the organ-protecting layer comprising a first and a second side, and the first side being intended for application to a wound base, more particularly exposed internal organs or the greater omentum, and the second side comprising a joining means, making it possible, after laying the organ-protecting layer on the wound base, more particularly exposed internal organs or the greater omentum, to establish a connection with a further bandage ply.

A further aspect in the context of the invention concerns a third product for use in the therapeutic treatment of the open abdomen on the human or animal body by means of negative pressure. The third product comprises a joining means which is used to avoid complications during the therapeutic treatment. Here, the third product is thus expressly claimed in connection with its specific medical indication, viz. avoiding complications or adverse effects during the negative-pressure treatment of the open abdomen. In this aspect, the joining means can join a first bandage ply which serves as an organ-protecting layer and which is intended for application to a wound base, more particularly exposed internal organs or the greater omentum, to a second bandage ply which is intended for application to the first bandage ply. The complication to be avoided in this aspect of the invention is the first bandage ply slipping out of place with respect to the second bandage ply during the therapeutic treatment.

The invention therefore also provides a joining means for use in the therapeutic treatment of the open abdomen on the human or animal body by means of negative pressure, it being possible for the joining means to join a first bandage ply which serves as an organ-protecting layer and which is intended for application to a wound base, more particularly exposed internal organs or the greater omentum, to a second bandage ply which is intended for application to the first bandage ply, characterized in that the joining means is indicated for the avoidance of a complication occurring during the treatment, the complication being the adhesive bonding of the second bandage ply to exposed internal organs or the adhesive bonding of the second bandage ply to the greater omentum as a consequence of movement of the first bandage ply with respect to the second bandage ply during the therapeutic treatment.

Furthermore, the invention concerns a fourth product for use in the therapeutic treatment of the open abdomen on the human or animal body by means of negative pressure. The fourth product comprises a joining means which is used to simplify the therapeutic treatment of the open abdomen on the human or animal body by means of negative pressure. Here, the fourth product is thus expressly claimed in connection with a further specific medical indication, viz. simplifying the therapeutic treatment of the open abdomen. In this aspect, the joining means can join a first bandage ply which serves as an organ-protecting layer and which is intended for application to a wound base, more particularly exposed internal organs or the greater omentum, to a second bandage ply which is intended for application to the first bandage ply. The claimed simplification of the therapeutic treatment of the open abdomen consists in it being possible to easily and safely remove the first bandage ply from the abdominal space after completion of the negative-pressure therapy by taking out the second bandage ply joined to the first bandage ply.

The invention therefore also provides a joining means for use in the therapeutic treatment of the open abdomen on the human or animal body by means of negative pressure, it being possible for the joining means to join a first bandage ply which serves as an organ-protecting layer and which is intended for application to a wound base, more particularly exposed internal organs or the greater omentum, to a second bandage ply which is intended for application to the first bandage ply, characterized in that the joining means simplifies the treatment by making it possible to easily and safely remove the first bandage ply from the abdominal space after completion of the negative-pressure therapy by taking out the second bandage ply joined to the first bandage ply.

The invention equally concerns a method for therapeutically treating the open abdomen on the human or animal body by means of negative pressure, comprising
  providing a negative-pressure source and optionally a container for the aspirated wound fluids,
  providing a suitable means for establishing communication of negative pressure between negative-pressure source and wound space, for example a negative-pressure line and a negative-pressure connecting piece (port),
  providing a suitable means for sealing the wound space, for example an airtight covering film,
  providing a first bandage ply having a first and a second side,
  providing a second bandage ply having a first and a second side,
  providing a joining means by means of which the second bandage ply can be permanently or temporarily joined to the first bandage ply,
  laying the first side of the first bandage ply on a wound base, more particularly exposed internal organs or the greater omentum,
  laying the first side of a second bandage ply on the second side of the first bandage ply,
  establishing a permanent or temporary connection between first bandage ply and second bandage ply,
  optionally applying further bandage plies,
  establishing airtight covering of the abdominal space and connection of a negative-pressure source,
  carrying out the negative-pressure therapy.

The presently proposed apparatuses, products, bandage components and methods can be used with customary apparatuses for negative-pressure wound therapy that are known to a person skilled in the art. Such apparatuses for negative-pressure wound therapy that are known from the prior art comprise, for example, a negative-pressure source, a container for accommodating the exudate aspirated from the wound space, one or more conducting means, a negative-pressure connecting piece, and an airtight, self-adhesive film for sealing the wound space.

The presently introduced apparatus comprises at least two bandage plies which are provided separately before use.

The first bandage ply is a fluid-permeable organ-protecting layer which is intended for application to or placement on a wound base, more particularly for application to or placement on exposed internal organs or the greater omentum. After placement of the central region of the organ-protecting layer, the edge region of the organ-protecting layer is usually introduced into the gap formed by abdominal wall and internal organs. By this means, undesired adhesive bonding of organs or the greater omentum to the abdominal wall shall be prevented. The organ-protecting layer preferably comprises a fluid-permeable textile material or a fluid-permeable flexible film composed of a polymeric material, more particularly a flexible, perforated film. It is essential that the organ-protecting layer consists of a material which, over the period of use, does not adhesively bond to or grow together with the exposed internal organs, the greater omentum or the abdominal wall. The material shall have atraumatic properties. Preferably, the organ-protecting layer comprises a film, more particularly a thermoplastic film. Suitable materials for a thermoplastic film comprise, in particular, ethylene-vinyl acetate (EVA), polyurethane (PU), polyethylene (PE), polyethylene terephthalate (PET), polytetrafluoroethylene (PTFE), polyvinyl chloride (PVC), thermoplastic elastomers (TPE), polyorganosiloxane (silicone) or a mixture thereof. In this connection, the name TPE encompasses olefin-based thermoplastic elastomers (TPO), crosslinked olefin-based thermoplastic elastomers (TPV), urethane-based thermoplastic elastomers (TPU), thermoplastic polyester elastomers or thermoplastic copolyesters (TPC), styrene block copolymers (TPS) and thermoplastic copolyamides (TPA). Preferably, the thermoplastic film is a polyethylene film.

The basis weight of the first film should be at least 30 g/m$^2$ and not more than 150 g/m$^2$, preferably at least 45 g/m$^2$ and not more than 95 g/m$^2$ and in particular at least 55 g/m$^2$ and not more than 65 g/m$^2$.

Normally, the organ-protecting layer is present as a single-ply material layer. However, it is also alternatively possible to use, as organ-protecting layer, a multilayer structure, the different plies of which are joined in an undetachable and thus laminate-type manner. The different plies can be manufactured from the same or from different materials, which are then joined by the manufacturer to form a laminate. The first and/or second surface of the first bandage ply can contain a three-dimensional structure, for example perforations having three-dimensional edges. The thickness of the single-ply or multilayer organ-protecting layer is altogether, including any three-dimensional structures present on the surface, from 10 to 1000 μm, preferably from 20 to 500 μm.

After application of the first bandage ply, the first side of the second bandage ply is applied to the second side of the first bandage ply. Compared to the first bandage ply, the second bandage ply preferably has a smaller surface area; more particularly, the surface area of the first side of the second bandage ply is at least 3% and not more than 97%, in particular at least 25% and not more than 90%, of the surface area of the first side of the first bandage ply. The second bandage ply must be fluid-permeable and fluid-conductive, making it possible, firstly, to transport fluid aspirated from the wound toward the negative-pressure source and, secondly, to ensure uniform distribution of the negative pressure in the wound space. The second bandage ply further serves to uniformly distribute the mechanical pressure exerted on the wound base during the negative-pressure treatment. To this end, the second bandage ply should preferably be of a substantially greater thickness compared to the first bandage ply, for example from 2 mm to 100 mm, in particular from 5 mm to 50 mm. In practice, the second bandage ply is frequently applied such that the second bandage ply is arranged between the wound edges. This is especially required when a temporary wound closure is to be established. In this case, the thickness of the second bandage ply should match the thickness of the abdominal wall.

Suitable materials for producing the second bandage ply comprise textile or polymeric materials, more particularly a foam composed of polyurethane, a foam composed of silicone or a foam composed of polyvinyl alcohol (PVA).

In a preferred embodiment of the invention, the second bandage ply comprises one or more layers of a porous polymer foam. An open-cell polymer foam is particularly suitable in this regard. In the context of this application, the term open-cell means that the foam contains at least 60% open cells, preferably at least 90% open cells, more preferably at least 98% open cells, in particular substantially 100% open cells, based on the total number of cells.

Suitable materials for a porous foam comprise, for example, polyurethane, polyurethane-polyurea copolymers, polyvinyl alcohol (PVA) or silicone.

As an alternative or in addition, the fluid-permeable layer can comprise textile materials such as wovens or nonwovens, for example a nonwoven fabric composed of synthetic polymers such as polyamide, polyester or polypropylene.

The second bandage ply can be single-ply, or comprise multiple layers. In the case of a second bandage ply comprising multiple layers, it is not necessary for the layers to be undetachably joined to one another. The individual layers can be held ready separately and applied successively. For example, it is possible for multiple plies of a porous foam to be applied successively until the second foam ply is of a thickness which is adequate according to the judgment of the physician performing the treatment.

According to the invention, the apparatus comprises a joining means by means of which the second bandage ply, after application of the first ply to the wound base, more particularly exposed internal organs or the greater omentum, can be joined to the first bandage ply. In the context of the present invention, joining means is understood to mean any means which ensures permanent or temporary joining of first and second bandage ply.

The joining means can be present on the first and/or on the second bandage ply or be an integral part of first and/or second bandage ply. Alternatively, the joining means can be a means which is separate from first and/or second bandage ply. The joining means comprises means for connection with a form fit, means for connection with a force fit and means for integral bonding. Nonlimiting examples for form-fit joining means usable in the context of the present invention comprise snap-fitting means, hooking means, surface structures complementary to one another, or zippers. Preferred form-fit joining means comprise, for example, mutually linking surface elements or separately applied hook-and-loop elements. Nonlimiting examples for force-fit joining means usable in the context of the present invention comprise material strips or ribbons which can be knotted together and clamps. Nonlimiting examples for integral-bonding joining means usable in the context of the present invention comprise adhesive or sticking surfaces and separately applied adhesives, adhesive strips or adhesive layers.

Joining means particularly preferred in the context of the present invention comprise, in particular, hook-and-loop elements applied to the second side of the first bandage ply and/or to the first side of the second bandage ply and also material strips, ribbons or threads which are present on the first bandage ply and on the second bandage ply and can be knotted or sewn together. Further particularly preferred joining means comprise three-dimensional structures which are present on the surface of the second side of the first bandage ply and on the surface of the first side of the second bandage ply and which bring about adhesion between the two surfaces.

The joining means can comprise a plurality of individual joining elements. The joining means enables the user, i.e. for example the physician performing the treatment, to establish detachable or undetachable joining of first bandage ply and second bandage ply after application of the first bandage ply, making it possible to avoid movement of the first bandage ply with respect to the second bandage ply as far as possible during the negative-pressure therapy. In practice, it has additionally been found that an apparatus according to the invention can be removed from the wound space with particular ease because the initially separately applied bandage plies adhere to one another during bandage change. It is therefore not necessary to detach the organ-protecting layer and the further ply individually. This facilitates handling of the bandage during bandage change.

An advantage of the present invention compared to a laminate made by a manufacturer and composed of first and second bandage ply is that the detachable or undetachable joining of first bandage ply and second bandage ply only comes about after application of the first bandage ply. Therefore, both bandage plies can be independently tailored to the wound proportions and applied.

In principle, in the context of the present invention, it is possible to use joining means which, after application of the second bandage ply to the second surface of the first bandage ply, make it possible to establish permanent and undetachable joining of first and second bandage ply. Similarly, it is possible to use joining means which, after application of the second bandage ply to the second surface of the first bandage ply, bring about only temporary and detachable joining of first and second bandage ply, so long as sufficient adhesion of first and second bandage ply is ensured for the duration of negative-pressure application, making it possible to avoid movement of the first bandage ply with respect to the second bandage ply as far as possible during the therapy. Sufficient adhesion of first and second bandage ply is ensured in particular when a static sliding friction force $F_s$ of at least 3 N, preferably at least 5 N, is required in order to move the first bandage ply against the second bandage ply in the wet state and/or when a static sliding friction force $F_s$ of at least 6 N, preferably at least 9 N, is required in order to move the first bandage ply against the second bandage ply in the dry state (both measured in accordance with DIN EN ISO 8295, as shown in more detail in the exemplary embodiment). Since the sliding friction force present between the surfaces can, for manufacturing reasons, vary in the longitudinal direction ("machine direction", also referred to as "MD")

and transverse direction of the materials, an "at least required static sliding friction force $F_s$" is understood here to mean the minimum static sliding friction force $F_s$ occurring in the case of different orientations of the plies to one another. This can ensure that it is possible to avoid as far as possible movement of the first bandage ply with respect to the second bandage ply during the therapy in all directions and independently of the orientation of the plies to one another.

In a preferred embodiment, the apparatus according to the invention comprises a first bandage ply, a second bandage ply and a joining means as described above, wherein a static sliding friction force $F_s$ of at least 3 N is required in order to move the first bandage ply in the wet state against the second bandage ply in the wet state and/or wherein a static sliding friction force $F_s$ of at least 6 N is required in order to move the first bandage ply in the dry state against the second bandage ply in the dry state.

In the context of the present invention, embodiments according to which the joining means is present in particular on the second side of the first bandage ply are conceivable. In a particularly preferred embodiment, the apparatus therefore comprises an organ-protecting layer, more particularly a flexible film as organ-protecting layer, having a first and a second side, for use in the negative-pressure therapy of the open abdomen, the first side being intended for application to exposed internal organs or to the greater omentum and the second side comprising a joining means, making it possible, after laying the organ-protecting layer on exposed internal organs or on the greater omentum, to establish a connection with a further bandage ply. In the context of said preferred embodiment, film strips, ribbons or threads can be present in particular on the first bandage ply and these, after application of the further bandage ply, can be joined to the further bandage ply. To this end, the film strips, ribbons or threads can, for example, be sewn or knotted together with the further bandage ply. It is also conceivable for slits to be provided by the manufacturer on the further bandage ply, through which slits the film strips, ribbons or threads can be passed through in order to join the first bandage ply to the further bandage ply. It would likewise be conceivable for the user to introduce into the second bandage ply immediately before application of the second bandage ply openings or cuts at an appropriate site, through which one or more free ends of the film strips, ribbons or threads can be passed through and, if necessary, knotted.

Alternatively, the second side of the first bandage ply can comprise an adherent or adhesive surface, making it possible to establish, after application of the further bandage ply, an adhesive connection between first bandage ply and further bandage ply. The adhesive connection should be in such a way that a static sliding friction force $F_s$ of at least 6 N is required in order to move the first bandage ply in the dry state against the second bandage ply in the dry state. In a preferred embodiment, it is therefore possible for the joining means to be present only on the second side of the first bandage ply. In this case, joining of first and second bandage ply is brought about solely by a joining means present on the first bandage ply, the joining means preferably being present on the surface of the second side of the first bandage ply.

In a further preferred embodiment which, in the context of the invention, is of particular significance in medical practice, the joining means comprises both the surface of the second side of the first bandage ply and the surface of the first side of the second bandage ply. Here, it is envisaged in particular that the surface of the second side of the first bandage ply and the surface of the first side of the second bandage ply comprise three-dimensional structures (also referred to as 3D structures) which bring about adhesion between the two surfaces. In said embodiment, any type of three-dimensional surface structure can, in principle, be functionalized in a manner that joins the bandage plies, so long as the structures can achieve during the negative-pressure therapy a form-fit or force-fit connection of first and second bandage ply that is temporary or permanent. Here, it is not absolutely necessary for the structures used in a joining function to be solely or primarily applied for avoiding as far as possible movement of the first bandage ply with respect to the second bandage ply and/or for simultaneously removing first and second bandage ply during bandage change. It would be equally conceivable for the surface structures bringing about a form-fit or force-fit connection to be present on the surface with respect to further functions not explained here in more detail, insofar as and so long as it is possible for the user to establish a temporary or permanent connection between first and second bandage ply, after he has applied the second bandage ply to the first bandage ply.

Three-dimensional structures present on the surface of the second side of the first bandage ply and the surface of the first side of the second bandage ply can be an integral part of the bandage ply, or be applied to both surfaces by the manufacturer as a separate component. Nonexclusive examples of a three-dimensional structure applied separately to a surface by the manufacturer which are proposed here are hook-and-loop elements undetachably applied to the bandage ply in a striped, annular or punctiform manner and also film strips or ribbons undetachably fixed to the surface of the bandage ply. Nonexclusive examples of a 3D structure which can be an integral part of the bandage ply which are proposed here are a three-dimensional perforation in a film and also a three-dimensional surface of an open-cell foam. In the case of the aforementioned perforated film which can be used in the context of the invention particularly as an organ-protecting layer, the three-dimensionally introduced perforations can, for example, protrude as craters from the plane of the film, forming a microstructure which can form an adhesive connection with a suitable opponent in the second bandage ply. With respect to the open-cell foam which is likewise mentioned by way of example and which is a possibility in the context of the invention preferably as a second bandage ply, the adhesion-permitting three-dimensional microstructure can be provided by the struts of the foam cells and/or by cavities open toward the surface of the foam. To achieve the desired adhesive effect, care must be taken when selecting the foam material used to produce the second bandage ply that a sufficient proportion of foam struts is present on or close to the foam surface and is therefore exposed to access by adhesive microstructures of the first bandage ply and/or that a sufficient number of cavities open toward the surface of the foam is present. The struts are substantially present within the foam body, and so they typically do not protrude beyond the plane of the three-dimensionally structured foam surface. A hooking or other form-fit interaction of the three-dimensional structures present on the surface of the first bandage ply with the microstructures on the surface of the second bandage ply, viz. the perforation edges and the struts of the foam, can only take place when the participating structural elements are coordinated with one another in terms of their dimensions. Alternatively or additionally, i.e. in an adhesion-strengthening manner, an adhesive interaction with the three-dimensional microstructures present on the first bandage ply can be achieved by a multiplicity of cavities open toward the first surface of the foam, into which the microstructures present on the second side of the first bandage ply can penetrate, forming a form-fit and/or force-fit connection. Viewed at the microscopic level, the surface of an open-cell polymer foam comprising a multiplicity of cavities open toward the surface of the foam has a three-dimensional surface structure. The cavities open toward the surface are cells which are present in the interior of the foam and which are partially exposed by cutting of the foam that is required during the production of the bandage ply. To achieve an adhesive interaction between the microstructures present on the first bandage ply and the cavities present on the second bandage ply, it is likewise necessary for the microstructures present on both bandage plies and the cavities open toward the surface of the foam to be coordinated with one another in terms of their dimensions. A cell is the individual hollow space which is formed during the production of foams and which is partly or completely enclosed by cell walls and/or cell struts. A closed cell is typically a cell which is completely enclosed by its walls and therefore not connected with other cells via the gas phase. An open cell is typically a cell which is connected with other cells via the gas phase. In the context of this application, the term open-cell means that the foam contains at least GO % open cells, preferably at least 90% open cells, more preferably at least 98% open cells, in particular substantially 100% open cells, based on the total number of cells. The proportion of open cells in the foam is typically determined in accordance with ASTM D 2856-87, method B). Cell wall is typically understood to mean the wall enclosing the cell. The cell wall can also be referred to as a cell membrane. Cell strut or strut is typically understood to mean the region of the cell wall which separates more than two cells from one another. The open-cell foam preferably usable in the context of the invention as a second bandage ply can be a reticulated or nonreticulated foam. A reticulated foam is understood to mean a foam which substantially comprises only struts. In the case of a reticulated foam, the cell walls are therefore substantially removed.

In a particularly preferred embodiment, the first bandage ply, i.e. the organ-protecting layer, is a flexible, perforated film, more particularly a film composed of polyethylene, which comprises three-dimensional perforations. As already described, it has been found here to be particularly advantageous when the perforations are introduced into the film such that the edges protrude from the second surface of the film, and so a three-dimensional structure, more particularly a crater-shaped structure, is present on the second surface of the film. It is important here that the preferably crater-shaped structure protrudes beyond the planar surface of the film to an extent that allows adhesion. However, the structure should not protrude too far from the surface, since otherwise the strength of the hooking microstructures may lessen. The structure is therefore preferably of a height of at least 100 μm and not more than 2000 μm, in particular of at least 200 μm and not more than 1000 μm and very particularly preferably of at least 250 μm and not more than 600 μm. The height is understood here to mean the maximum extent of the three-dimensional structure that is measured perpendicularly with respect to the plane of the film. The measurement can be done on the basis of suitable micrographs of film cross sections. In addition, the adhesion effect of the microstructures formed by the perforation is affected by the angle formed by the plane of the crater walls against the plane of the planar film. It has been found here that it is possible to observe effective adhesion in particular when said angle is at least 10° and not more than 90°, preferably at least 45° and not more than 80°.

In a further particularly preferred embodiment already mentioned above in connection with an example, the second bandage ply is an open-cell polymer foam which has, on its first surface, a multiplicity of cavities open toward the first surface and also a multiplicity of struts, making it possible for the structures present on the surface of the first bandage ply to interact in an adhesive manner with the structures present on the surface of the second bandage ply. In said embodiment, the structures present on the surface of the second bandage ply are thus, for example, cavities or the struts of the foam.

In an embodiment which is very particularly preferred here, the apparatus comprises, as first bandage ply, a flexible, perforated film having 3D microstructures and also, as second bandage ply, an open-cell polymer foam. The film has as organ-protecting layer a first and a second side, the first side being intended for application to the wound base. Here, the 3D microstructures protrude solely from the second surface, and so the second surface has a rough quality, whereas the first surface has a mostly smooth quality. Furthermore, the apparatus comprises in said embodiment an open-cell polymer foam having a first and a second side, the first side being intended for application to the second side of the organ-protecting layer. The polymer foam, which is preferably an open-cell foam composed of polyurethane, more particularly polyester polyurethane, has, on its first surface, cavities open toward the first surface. The apparatus further comprises joining means. These are microstructures present on the surface of organ-protecting layer and polymer foam, which microstructures bring about an adhesive interaction after contacting of the organ-protecting layer with the foam. Thus, the polymer foam can, after application of the organ-protecting layer to exposed internal organs or to the greater omentum, be joined in an adhesive manner to the organ-protecting layer merely by contacting, making it possible to avoid movement of the first bandage ply with respect to the second bandage ply as far as possible during the therapy and/or facilitating simultaneous removal of first and second bandage ply. In the context of the embodiment which is described here and which comprises a film and a foam, it has been found to be particularly advantageous with respect to adhesion when the first and the second bandage ply have the following features in combination:

a) The first bandage ply (organ-protecting layer) comprises a transparent, three-dimensionally perforated film composed of polyethylene. The perforation edges protrude as funnels from the second side of the film. The height of the three-dimensional funnel-shaped structure present on the second side is from 250 μm to 600 μm. The thickness of the film (material thickness) is from 10 μm to 100 μm. The open surface of the perforations present in the film is at least 19% and not more than 23%, preferably at least 20% and not more than 22%, of the surface extent of the film. The number of openings present in the first film per unit area is at least 270 per $cm^2$ and not more than 290 per $cm^2$. The diameter of the perforations, measured in the plane of the film, is at least 250 μm and not more than 350 μm. The basis weight of the film, measured in accordance with EN ISO 2286-2, is at least 55 $g/m^2$ and not more than 65 $g/m^2$.

b) The second bandage ply comprises an open-cell foam, obtainable by reacting a mixture comprising the components (i) polyisocyanate, (ii) polyester polyol, (iii) blowing agent, and (iv) catalyst. The elongation at break of the foam, measured in accordance with DIN 53571, is from 280% to 300%. The foam has a cell count (=number of pores along a straight line laid out on the foam surface in the machine direction per cm) of from 8 to 15 per cm. The cell count is preferably determined microscopically. The foam has a bulk density, measured in accordance with DIN EN ISO 845 (test specimen having dimensions of 100 mm×100 mm×50 mm, conditioning for 24 h in a standard atmosphere (23° C., 50% rel. air humidity, 1013 mbar)), of between 25.4 and 26.2 kg/m$^3$ and an air permeability, measured in accordance with DIN EN ISO 9237 (20 mm test thickness, 20 cm$^2$ test area, 200 Pa differential pressure), of from 2620 l/(m$^2$ sec) to 2740 l/(m$^2$ sec). A foam which is particularly highly suitable in the context of this embodiment is obtainable from a mixture comprising the components (i) polyisocyanate, (ii) polyester polyol, (iii) blowing agent, and (iv) catalyst, the polyester polyol being preferably obtainable by reacting a dicarboxylic acid having from 4 to 8 carbon atoms with a dialcohol having from 2 to 6 carbon atoms and/or preferably having a weight-average molecular weight of from 500 to 4000 g/mol.

When using a first bandage ply and a second bandage ply having the features mentioned above under a) and b), it is possible to achieve a static sliding friction force $F_s$ of at least 3 N being required in order to move the first bandage ply against the second bandage ply in the wet state and a static sliding friction force $F_s$ of at least 6 N being required in order to move the first bandage ply against the second bandage ply in the dry state. When using materials other than those proposed here, it may be necessary to optimize the sliding friction force by varying the parameters mentioned above under a) and b). Experiments of this type can be carried out without relatively huge effort starting from the parameter ranges already proposed here.

Unless otherwise indicated in the relevant standards, all test methods are generally carried out at 23° C., 50% rel. air humidity and 1013 mbar pressure.

For improved application of a flexible film which is intended for application to exposed internal organs or to the greater omentum and which can therefore act as an organ-protecting layer, the as yet unpublished European patent application EP11007377.2-2124 proposed that, on the film, at least one pocket which is predominantly open toward the center of the wound dressing be present on the side of the wound dressing that is facing away from the wound during use. The at least one pocket can considerably facilitate uniform application and laying out of the wound dressing on the wound base and is therefore likewise recommended for use in connection with the apparatuses, products and methods described here.

In the context of the invention, a bandage set is likewise claimed, comprising:

i) a first bandage ply having a first and a second side, as organ-protecting layer, the first side being intended for application to a wound base, more particularly exposed internal organs or the greater omentum, and the surface area of the bandage ply being from 2500 cm$^2$ to 4000 cm$^2$, in particular from 3200 cm$^2$ to 3500 cm$^2$, ii) a second bandage ply provided separately from the first bandage ply and having a first and a second side, the first side of the second bandage ply being intended for application to the second side of the first bandage ply, and the surface area of the second bandage ply being from 500 cm$^2$ to 2000 cm$^2$, in particular from 900 cm$^2$ to 1000 cm$^2$, iii) a joining means by means of which the second bandage ply, after application of the first ply to exposed internal organs or to the greater omentum, can be joined to the first bandage ply, making it possible to avoid movement of the first bandage ply with respect to the second bandage ply as far as possible during the therapy and/or facilitating simultaneous removal of first and second bandage ply, iv) optionally an airtight covering film for closing the wound space.

The joining means is preferably material pieces applied to the second side of the first bandage ply and/or to the first side of the second bandage ply, for example film strips or hook-and-loop elements. In an alternative, but equally preferred embodiment of the bandage set, the joining means is microstructures which are present on the second side of the first bandage ply and/or on the first side of the second bandage ply and which can bring about a static sliding friction force $F_s$ of at least 3 N being required in order to move the first bandage ply against the second bandage ply in the wet state and a static sliding friction force $F_s$ of at least 6 N being required in order to move the first bandage ply against the second bandage ply in the dry state.

Use Example I

When using the apparatus according to the invention for the negative-pressure therapy of large-area wounds in the abdominal region, a first bandage ply is firstly placed, as organ-protecting layer, on the portion of the wound base that is accessible to the user. The first bandage ply is preferably a perforated film comprising three-dimensional structures on its surface that is facing away from the wound during use. The edge of the first bandage ply is then inserted into the gap formed by abdominal wall and wound base to a depth of approximately 1 cm to 15 cm. The wound dressing therefore forms a wound fluid-permeable protective layer for the exposed internal organs. A second bandage ply having a thickness extent of 3 cm is applied to the organ-protecting layer in the region between the wound edges. In this connection, it is very beneficial for wound healing when the second bandage ply is tailored to the shape of the wound in such a way that the wound edges are in complete contact with the second bandage ply. The surface area of the second bandage ply is therefore lower than the surface area of the first bandage ply. The second bandage ply is, in particular, a porous polymer foam which has open cells on its surface, and so the foam struts can interact in an adhesive manner with the three-dimensional structures of the perforated film (organ-protecting layer) after contacting of the surfaces of first and second bandage ply.

For airtight closure of the wound region, an air-impermeable covering material is placed over the wound. The edges of the covering material are stuck onto the intact skin. Furthermore, a negative-pressure connecting piece is applied to establish functional connection of the wound space to a negative-pressure source situated beyond the covering material, for example a negative-pressure pump, making it possible to establish negative pressure in the wound space and to aspirate fluids from the wound space. The negative-pressure connecting piece is preferably stuck onto the external side of the covering material that is facing away from the wound, a suitable opening being cut into the otherwise air-impermeable covering material before the piece is stuck. The negative-pressure therapy is initiated by connecting the negative-pressure connecting piece to a negative-pressure source and applying a preferably constant negative pressure for a period ranging from a few minutes up to several days.

A preferred negative pressure is the range of at least 80 mmHg to not more than 250 mmHg, preferably 125 mmHg.

The adhesive connection of first and second bandage ply ensures that movement of the first bandage ply with respect to the second bandage ply can be avoided as far as possible during the therapy.

Use Example II

When using the apparatus according to the invention for the negative-pressure therapy of large-area wounds in the abdominal region, a first bandage ply is firstly placed, as organ-protecting layer, on the portion of the wound base that is accessible to the user. The first bandage ply is preferably a perforated film, and on its surface that is facing away from the wound during use, 6 film strips have been applied by the manufacturer, distributed across the surface. The film strips are each 20 cm in length and 1 cm in breadth. The film strips are undetachably joined in their center, by means of a punctiform welded connection, to the organ-protecting layer, and so the film strips have free ends, each approximately 10 cm in length. The edge of the first bandage ply is then inserted into the gap formed by abdominal wall and wound base to a depth of approximately 1 cm to 15 cm. The wound dressing therefore forms a wound fluid-permeable protective layer for the exposed internal organs. A second bandage ply having a thickness extent of 5 cm is applied to the organ-protecting layer in the region between the wound edges. The second bandage ply is, in particular, a porous polymer foam which has, distributed across its surface, slits passing through the entire thickness extent of the foam. The slits are each 3 cm in length. The foam has 5 slits per area of 100 cm². Two to five free ends of the film strips present on the first bandage ply are passed through the slits of the second foam ply and knotted together on the surface that is facing away from the wound, ensuring firm joining of first and second bandage ply during the negative-pressure treatment. In this connection, it is very beneficial for wound healing when the second bandage ply is tailored to the shape of the wound in such a way that the wound edges are in complete contact with the second bandage ply. The surface area of the second bandage ply is therefore lower than the surface area of the first bandage ply.

For airtight closure of the wound region, an air-impermeable covering material is placed over the wound. The edges of the covering material are stuck onto the intact skin. Furthermore, a negative-pressure connecting piece is applied to establish functional connection of the wound space to a negative-pressure source situated beyond the covering material, for example a negative-pressure pump, making it possible to establish negative pressure in the wound space and to aspirate fluids from the wound space. The negative-pressure connecting piece is preferably stuck onto the external side of the covering material that is facing away from the wound, a suitable opening being cut into the otherwise air-impermeable covering material before the piece is stuck. The negative-pressure therapy is carried out as described in use example I.

The joining of first and second bandage ply that is brought about by the film strips ensures that movement of the first bandage ply with respect to the second bandage ply can be avoided as far as possible during the therapy.

During bandage change, the first and the second bandage ply can be removed in a single operation, since the first and the second bandage ply are firmly joined to one another.

Determination of Sliding Friction Force $F_s$

The static sliding friction force $F_s$ of a film surface against a foam surface was determined analogously to DIN EN ISO 8295 (October 2004 edition) using the test instrument described in the standard (tensile test machine from Zwick, Germany), with a level test table being used. Three samples were measured in each case and the mean was calculated from the three measurements. For measurement of the samples in the dry state, conditioning was carried out before the test for at least 16 h in a standard atmosphere at 23° C., 50% relative air humidity, 1013 mbar. For measurement of the samples in the wet state, the samples (foam and film) were completely immersed in water. Thereafter, the samples were held vertically for 30 s to allow dripping and clamped into the test instrument. The foam ply (dimensions 150×300 mm) was fixed on the test table, whereas the film ply (dimensions 65×200 mm) was clamped into the sled. The period between dripping and the start of measurement was no greater than 2 min. The square contact footprint of the sled covered with the film was 40 cm². The sled was drawn across the immobile test table. The test speed was 100 mm/min. The weight of the traction sled including the friction block was 200 g. The prestress between sled and force measurement instrument was 0.2 N.

EXAMPLE

Determination of the Sliding Friction Force of a First Bandage Ply Against a Second Bandage Ply on a Test Instrument The static sliding friction force $F_s$ was determined, as described above, analogously to DIN EN ISO 8295.

Sample Pair 1—Open-cell foam against a slit film having a largely smooth surface.

Foam: Hydrophobic polyester polyurethane foam. Bulk density as per ISO 845 of 25.8 kg/m³, compressive strength as per DIN EN ISO 3386-1 of 3.9 kPa, tensile strength as per DIN 53571 A of 170 kPa, elongation at break as per DIN 53571 A of 290%, cell count (determined microscopically on a straight line laid out on the surface of the foam) of 11/cm, air permeability as per DIN EN ISO 9237 of 2680 l/m²s. A foam of this type that is usable as wound dressing is commercially available under the name VivanoMed® Foam (Paul Hartmann AG, Germany).

Film: Smooth, transparent polyurethane film having slits. Approximately 20 slits distributed across the surface of the film, each slit 4.5 mm in length, were introduced into the film per 100 cm² of film surface. The slits were aligned in parallel to the machine direction (MD) of the film. When using a film of this type as wound contact layer or organ-protecting layer, the slits serve to conduct wound exudate. The use of slitted films as wound contact layer, especially in the context of negative-pressure therapy, is known from the prior art.

The film was clamped into the measurement sled in such a way that the sled moved along the machine direction of the film.

Sample Pair 2—Open-cell foam against a slit film comprising a three-dimensional crater-shaped structure on one surface.

Foam: Hydrophobic polyester polyurethane foam. Bulk density as per ISO 845 of 25.8 kg/m³, compressive strength as per DIN EN ISO 3386-1 of 3.9 kPa, tensile strength as per DIN 53571 A of 170 kPa, elongation at break as per DIN 53571 A of 290%, cell count (determined microscopically on a straight line laid out on the surface of the foam) of 11/cm, air permeability as per DIN EN ISO 9237 of 2680 l/m²s. A foam of this type that is usable as wound dressing is commercially available under the name VivanoMed® (Paul Hartmann A G, Germany).

Film: Transparent polyethylene film rough on one side and having perforations. The film comprises about 280 perforations per cm² of film surface, each perforation having a diameter of 0.3 mm. The perforations were introduced into the film in such a way that the perforation edges protrude from the second surface of the film, and so a crater-shaped, three-dimensional structure is present on the second surface. By contrast, the first surface of the film is largely smooth. The open surface area of the film is 21%. The film was clamped into the measurement sled in such a way that the sled moved along the machine direction (MD) of the film. The rough side of the film (second surface) was aligned toward the test table, and so the rough side was in contact with the foam.

The static sliding friction force present between the material plies (sample pairs) was determined in each case for dry and wet samples by means of the measurement method specified above. The mean values of the measured sliding friction force Fs from three measurements in each case are reported below.

| | |
|---|---|
| Sample pair 1-dry | 0.98N |
| Sample pair 1-wet | 0.72N |
| Sample pair 2-dry | 10.08N |
| Sample pair 2-wet | 5.86N |

REFERENCE SIGNS

1 Negative-pressure source
2 Canister for wound exudate
3 Wound base, more particularly exposed internal organs or the greater omentum
4 Abdominal wall
5 Wound edge
6 Airtight covering film for sealing the wound space
7 Negative-pressure connecting means (port)
8 Negative-pressure line
9 Opening in covering film
10, 20 Apparatus, placed on an abdominal wound, for use in the therapeutic treatment of the open abdomen on the human or animal body by means of negative pressure
11, 21, 31 Perforated, flexible film (organ-protecting layer)
12, 22 Open-cell polymer foam
13 Hollow space in the open-cell polymer foam that is open toward the surface
14 Foam strut present on or close to the first surface of the open-cell polymer foam
15 Perforation in the flexible film
16 Perforation edge in the flexible film. The perforation edge protrudes from the second surface of the film, forming a three-dimensional structure on the second surface of the film
25 Hook-and-loop element undetachably attached to the second side of the perforated, flexible film
26 Hook-and-loop element undetachably attached to the first side of the open-cell polymer foam
27, 33 Opening in the flexible film
30 Organ-protecting layer having pockets and film strip
31 Perforated film
35 Film strip attached to the second side of the first bandage ply
38 Pocket open toward the center of the film
39 Fixation point

FIGURES

The wound dressing or apparatus according to the invention for negative-pressure wound therapy will now be more particularly elucidated with reference to diagrammatic drawings (not true to scale). However, the invention is not to be understood to be reduced to the embodiments depicted in the drawings or in the description of the drawing. On the contrary, the invention also encompasses combinations of the individual features of the alternative forms.

FIG. 1a shows the transverse section of a preferred embodiment of an apparatus, placed on an abdominal wound, for use in the negative-pressure therapy of the open abdomen.

FIG. 1b shows a drawing adapted from a micrograph (REM) of an open-cell polymer foam suitable as second bandage ply, in plan view of the first side. The figure therefore shows a surface detail (original size 6 mm×6 mm) of ply 12 from FIG. 1a.

FIGS. 1c/d show drawings adapted from micrographs (reflected-light microscope) of a perforated film suitable as first bandage ply, in plan view of the second side (FIG. 1c; original size approximately 23 mm×23 mm) and from the side (FIG. 1d; original size approximately 9 mm×9 mm). The figures therefore show a surface detail present on the second side of ply 11 from FIG. 1a.

FIG. 1e shows a diagram of the surface detail from FIG. 1d.

FIG. 2a shows the transverse section of a further preferred embodiment of an apparatus, placed on an abdominal wound, for use in the negative-pressure therapy of the open abdomen.

FIG. 2b shows the first bandage ply from FIG. 2a, in plan view of the second side.

FIG. 2c shows the second bandage ply from FIG. 2a, in plan view of the first side.

Figure 3A:
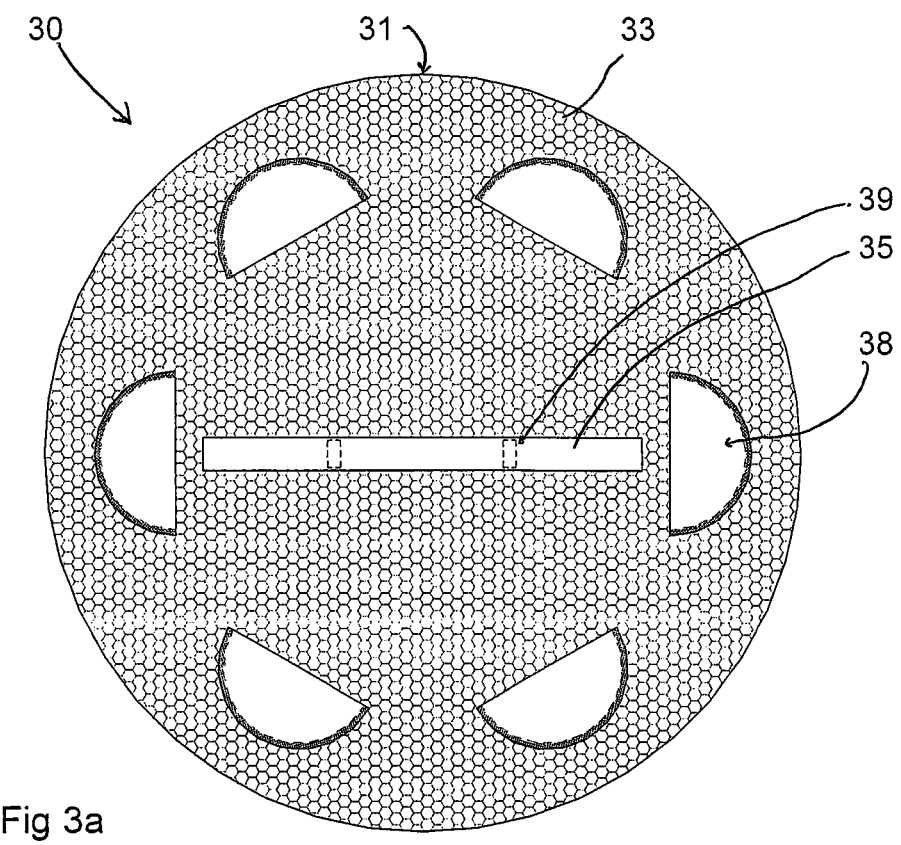
Figure 3B:
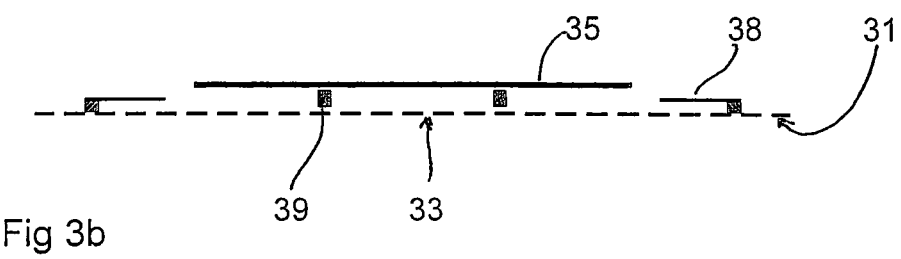

FIGS. 3a/b show a further embodiment of a first bandage ply, in plan view of the second side (FIG. 3a) and in transverse section (FIG. 3b).

DETAILED DESCRIPTION OF THE INVENTION

FIGS. 1 to 3 depict, by way of example, preferred embodiments of the invention. Common to the embodiments selected to illustrate the general idea of the invention is the fact that the apparatuses (10, 20, 30) shown comprise the joining means essential to the invention, by means of which joining means the second bandage ply (12, 22), after application of the first ply (11, 21, 31) to exposed internal organs or to the greater omentum, can be joined to the first bandage ply, making it possible to avoid movement of the first bandage ply (11, 21, 31) with respect to the second bandage ply (12, 22) as far as possible during the therapy and/or facilitating simultaneous removal of first and second bandage ply. It is clear from the examples depicted in FIGS. 1 to 3 that the joining means can be designed in a very wide variety of different ways, so long as it is ensured that it is possible for the second bandage ply, after application of the first ply to exposed internal organs or to the greater omentum, to be joined to the first bandage ply, making it possible to avoid movement of the first bandage ply (11, 21, 31) with respect to the second bandage ply (12, 22) as far as possible during the therapy and/or facilitating simultaneous removal of first and second bandage ply. Accordingly, it is clear to a person skilled in the art that a multiplicity of alternative joining means can be used in the apparatus according to the invention. In the exemplary embodiment according to FIG. 1, the joining means comprises three-dimensional structures which bring about adhesion between the surfaces of first and second bandage ply. In the exemplary embodiment according to FIG. 2, the joining means is realized by hook-and-loop elements present on the first and second bandage ply. By contrast, in the exemplary embodiment according to FIG. 3, there is, on the first bandage ply, merely a film strip which can be joined by the user to the second bandage ply. The embodiments described here clarify that the joining means can, for example, be present only on the first or only on the second bandage ply, as shown in FIG. 3 (the joining means 35, which is a film strip, is only present on the first bandage ply 31). Alternatively, both the first and the second bandage ply can comprise the joining means, as shown in the examples depicted in FIG. 1 and FIG. 2.

The diagram (not to scale) in FIG. 1a shows a preferred embodiment of the apparatus according to the invention on an abdominal wound. The wound comprises a wound base (3) and a wound edge (5) formed by the abdominal wall (4). In the case of an abdominal wound, the wound base (3) is usually exposed internal organs or the greater omentum. To start with, a flexible, perforated film (11) is applied as an organ-protecting layer to the wound base. Here, a first side of the film (11) is directly contacted with the wound base (3). The edges of the organ-protecting layer are inserted into the gap formed by wound base and abdominal wall. A reticulated polymer foam (12) tailored to the size of the wound, for example a polymer foam composed of polyurethane, is applied to the organ-protecting layer (11). Here, the foam is to be directly contacted with the wound edges (5). The thickness of the foam ply (12) should preferably match the thickness of the abdominal wall (4). The flexible film (11) comprises a multiplicity of three-dimensional perforations distributed across the surface of the film. The film (11) has a smooth first side and a roughened second side owing to the perforations (15) introduced into the film. FIGS. 1c and 1d show drawings adapted from micrographs of a perforated polyethylene film suitable for the embodiment depicted here, in plan view of the second side (FIG. 1c) and from the side (FIG. 1d). FIG. 1e shows a diagram of the surface detail from FIG. 1d. It can be seen from FIGS. 1c, 1d and 1e that there are microstructures (16) which protrude as craters from the plane of the film and which give the second surface of the film (11) a rough surface quality. The crater-type structures (16), which are approximately 400 μm in height (maximum extent of the three-dimensional structure, measured perpendicularly with respect to the plane of the film), are perforation edges. In the interior of the microstructures (16), there are openings or channels which penetrate the film. The diameter of the openings is, in each case, approximately 0.3 mm. The film shown in FIGS. 1a and 1c has an open surface of 21%, making it possible to ensure effective draining of the wound exudates released in the wound region during the therapy. FIGS. 1c and 1d therefore show a detail of the second surface of the flexible film (11) depicted only diagrammatically in FIG. 1a. FIG. 1b shows a drawing adapted from a micrograph of the surface of an open-cell polymer foam (12) which can advantageously form a second bandage ply in the embodiment shown here. In FIG. 1b, foam struts (14) and cavities (13) can be seen. The foam struts (14) and the cavities (13) form on the foam surface a three-dimensional microstructure which can form an adhesive connection with the crater-shaped microstructures (16) present on the second side of the flexible film (11) (in FIG. 1a, the adhesion between film and foam is indicated by the two-headed arrows), when the second surface of the film (11) is contacted with the first surface of the foam (12). In the embodiment shown in FIG. 1a, the joining means therefore comprises microstructures (13, 14, 15, 16) present on the second side of the first bandage ply (film 11) and on the first side of the second bandage ply (foam 12). Negative-pressure-tight covering of the wound area is achieved by applying the airtight covering film (6), which is fixed adhesively in the wound surroundings. Normally, the covering film (6) used for sealing the negative-pressure bandage is a polyurethane film coated with self-adhesive, for example the commercially available product Hydrofilm® (Paul Hartmann A G, Germany). An opening (9) having a diameter of approximately 0.5 cm is introduced into the covering film (6). A negative-pressure connecting means (port, 7), which is connected to a negative-pressure line (8), is fixed over the opening (9), making it possible to establish communication of negative pressure between the lumen of the negative-pressure line (8) and the wound space. After activation of the negative-pressure source (1), negative pressure can be established in the wound space and wound secretions can be sucked into the container (2).

The diagram (not to scale) in FIG. 2a shows a further preferred embodiment of the apparatus according to the invention on an abdominal wound. The apparatus comprises not only the covering film (6), port (7), negative-pressure line (8), canister (2) and negative-pressure source (1) components already depicted in FIG. 1, but also a film (21) having a largely smooth surface structure as an organ-protecting layer (first bandage ply) and a foam ply (second bandage ply 22) applied to the film (21), with both the film (21) and the foam ply (22) containing hook-and-loop elements (25, 26) which can join the first bandage ply (21) to the second bandage ply (22) by means of hook and loop (in FIG. 2a, the hook-and-loop connection established between film and foam is indicated by the two-headed arrows). Accordingly, the joining means according to the preferred embodiment shown in FIG. 2a comprises hook-and-loop elements (25, 26). The hook-and-loop joining of first bandage ply (21) and second bandage ply (22) ensures that the bandage plies are not moved with respect to one another during the negative-pressure therapy. In addition, simultaneous removal of organ-protecting layer (21) and foam ply (22) is facilitated after completion of the negative-pressure therapy. Preferably, the film (21) is a flexible polymer film, for example one composed of polyethylene. The film (21) has a multiplicity of openings (27) which are distributed across the surface of the film and which allow wound exudate to pass through. Here, the shape of the openings (27), for example circular or elliptical, is less crucial. However, it has been found in practice that the open surface of the film (21) should preferably be between 19% and 23% of the film surface in order to prevent adhesive bonding of the wound base (3) to the foam ply (22) and, at the same time, to ensure adequate draining of exudate. The second bandage ply preferably comprises a polymeric foam (22), more particularly an open-cell polyurethane foam. The hook-and-loop elements (25, 26) are undetachably attached by the manufacturer on the second side of the organ-protecting layer (21) that is facing away from the wound during use and also on the first side of the foam ply (22) that is facing the wound during use. The hook-and-loop elements (25, 26) should preferably be distributed across the surface of organ-protecting layer (21) and foam ply (22). At the same time, the hook-and-loop elements (25, 26) should allow wound exudate to pass through the organ-protecting layer (21) and through the foam ply with as little impediment as possible. Advantageously, the hook-and-loop elements (25, 26) can be attached to the organ-protecting layer (21) and/or to the foam ply (22) in a striped or circular arrangement. According to the preferred embodiment depicted in FIGS. 2b and 2c, the hook-and-loop elements (25) are applied to the second side of the organ-protecting layer (21) in a circular arrangement, whereas the hook-and-loop elements (26) are present on the first side of the foam ply (22) in a striped arrangement. Such an arrangement has been found to be particularly advantageous, since hook-and-loop joining of the bandage plies can be established independently of the orientation of the plies to one another. Here, it is equally possible for the hook-and-loop elements (25) to be applied to the second side of the organ-protecting layer (21) in a striped manner, while the hook-and-loop elements (26) are present on the first side of the foam ply (22) in a circular arrangement. Particularly preferably, the hook-and-loop elements are present on a bandage ply (first or second bandage ply) in the form of two or more concentrically arranged rings, as depicted exemplarily in FIG. 2b.

FIGS. 3a and 3b show a further embodiment of an organ-protecting layer (31) usable in the context of the present invention. The organ-protecting layer (31) is a flexible polymer film which has a largely smooth surface and which has a multiplicity of openings (33) to ensure that wound exudate passes through. On the second side of the organ-protecting layer (31) that is facing away from the wound during use, there is at least one film strip (35) which allows joining of the foam ply (not depicted in FIGS. 3a and 3b) to the organ-protecting layer (31). In addition, pockets (38) are present, as an application aid, on the second side of the organ-protecting layer (31) that is facing away from the wound during use. When using the product according to the invention, the organ-protecting layer (31) is, as already depicted in the context of FIG. 1a, firstly applied to the wound base, with the edges of the film (31) being inserted into the gap formed by wound base and abdominal wall. To facilitate uniform application and laying out of the organ-protecting layer (31) on the wound base, pockets (38) predominantly open toward the center of the film are present on the organ-protecting layer (31). The pockets (38) can comprise a bag-type material section, more particularly a bag-type film section, which, on the edge of the pocket (38), is undetachably fixed to the organ-protecting layer (31). Undetachable fixing of the material section forming a pocket (38) to the surface of the organ-protecting layer (31) can be achieved, for example, by adhesive bonding, welding or pressing. The user can introduce a planar surgical instrument, for example an abdominal and intestinal spatula, into the pocket (38) and then carefully insert under the abdominal wall the wound dressing held temporarily on the spatula by means of the pocket. After insertion of the edge region of the film (31) under the abdominal wall, the spatula is pulled out again from the pocket (38). Advantageously, the organ-protecting layer (31) comprises a multiplicity of pockets, for example six pockets (38), as depicted in FIG. 3a. A foam ply (not depicted in FIGS. 3a and 3b) tailored to the size of the wound is applied to the organ-protecting layer (31) applied to the wound base. The user can now join the at least one film strip (35) present on the organ-protecting layer (31) to the foam ply, and so movement of the organ-protecting layer (31) with respect to the second bandage ply is avoided as far as possible during the therapy and/or simultaneous removal of both bandage plies is substantially facilitated after the therapy. To this end, the film strip (35) can, for example, be sewn to the foam ply. Another possibility is that the user introduces into the foam ply small openings, through which one or more free ends of the at least one film strip (35) can be passed through. If necessary, the free ends of the film strips (35) can be knotted together or fixed in some other way on the side of the foam ply that is facing away from the wound. The at least one film strip can, for example, be fixed by means of fixation points (39) on the second side of the organ-protecting layer (31) that is facing away from the wound during use, as depicted in the transverse section in FIG. 3b. The fixation points (39) can, for example, be adhesion points or welding points. What is important in the embodiment shown here is that the at least one film strip (35) has at least one free end which, after application of the organ-protecting layer (31), can be joined to the further bandage ply, more particularly a foam ply.

According to a further embodiment not depicted here, it would also be possible for the second bandage ply to contain film strips, ribbons or threads which are joinable to the film strips present on the first bandage ply, for example by means of knot fastening.

The invention claimed is:

1. Apparatus suitable for use in negative-pressure therapy of an open abdomen, comprising
   a first bandage ply (11, 21, 31) having a first and a second side, as organ-protecting layer, the first side being intended for application to a wound base (3) wherein the first bandage ply comprises a fluid-permeable flexible film (11, 21, 31) composed of a polymeric material; and,
   a second bandage ply (12, 22) provided separately from the first bandage ply and having a first and a second side, the first side of the second bandage ply (12, 22) being intended for application to the second side of the first bandage ply, which second bandage ply (12, 22) does not come into direct contact with the wound base (3) wherein the second bandage ply comprises a fluid-permeable open-cell polymer foam (12, 22); and,
   three-dimensional structures (13, 14, 15, 16) on the surface of the second side of the first bandage ply (11) and the surface of the first side of the second bandage ply, which establish a detachable joining of first bandage ply and second bandage ply,
   wherein the three-dimensional structures on the surface of the first side of the second bandage ply comprise struts (14) present on or close to the surface of the first side of the second bandage ply, and also comprise cavities (13) open toward the surface, and wherein the cavities open towards the surface are cells which are present in the interior of the open-cell polymer foam and which are exposed and become the cavities open towards the surface by a cutting of the foam during the production of the second bandage ply and wherein the interior of the foam contains an intact cell structure which is not exposed by the cutting of the foam during the production of the second bandage ply, and
   wherein the three-dimensional structures on the surface of the second side of the first bandage ply are perforations (15) which are introduced into the film such that the perforation edges (16) protrude from solely the second surface of the film (11) to form crater-shaped structures on the second surface of the film (11) and the first surface of the first bandage ply is smooth, and
   wherein the crater-shaped structures present on the surface of the second side of the first bandage ply (11) can penetrate the cavities present on the surface of the second bandage ply (12) forming a form-fit and/or force-fit connection between the first bandage ply and the second bandage ply,
   such that the second bandage ply (12, 22), after application of the first ply (11, 21, 31) to the wound base (3), can be joined to the first bandage ply (11, 21, 31), so as to prevent movement of the first bandage ply (11, 21, 31) with respect to the second bandage ply (12, 22)

during the therapy and/or facilitates simultaneous removal of first (11, 21, 31) and second bandage ply (12, 22).

2. Apparatus according to claim 1, wherein the surface area of the first side of the second bandage ply (12, 22) is at least 3% and not more than 97%, of the surface area of the first side of the first bandage ply (11, 21, 31).

3. Apparatus according to claim 1, wherein a static sliding friction force $F_s$, measured in accordance with DIN EN ISO 8235, of at least 3 N is required in order to move the first bandage ply (11, 21, 31) in the wet state against the second bandage ply (12, 22) in the wet state and/or wherein a static sliding friction force $F_s$ of at least 6 N, measured in accordance with DIN EN ISO 8235, is required in order to move the first bandage ply (11, 21, 31) in the dry state against the second bandage ply (12, 22) in the dry state.

4. Apparatus according to claim 1, wherein the first bandage ply comprises a flexible film (31) and wherein, on the second side of the film (31), there is at least one pocket (38) which is predominantly open toward the center of the film and which facilitates uniform application and laying out of the film on the wound base.

5. The apparatus of claim 1 wherein the fluid-permeable open-cell polymer foam is a reticulated foam.

6. Bandage set suitable for use in negative-pressure therapy of an open abdomen, comprising
   i) a first bandage ply (11, 21, 31) having a first and a second side, as organ-protecting layer, the first side being intended for application to a wound base (3) and the bandage ply having a surface area of from 2500 cm² to 4000 cm², wherein the first bandage ply comprises a fluid-permeable flexible film (11, 21, 31) composed of a polymeric material; and,
   ii) a second bandage ply (12, 22) provided separately from the first bandage ply and having a first and a second side, the first side of the second bandage ply (12, 22) being intended for application to the second side of the first bandage ply (11, 21, 31), and the second bandage ply (12, 22) having a surface area of from 500 cm² to 2000 cm², which second bandage ply (12, 22) does not come into direct contact with the wound base (3) wherein the second bandage ply comprises a fluid-permeable open-cell polymer foam (12, 22); and,
   iii) three-dimensional structures (13, 14, 15, 16) on the surface of the second side of the first bandage ply (11) and the surface of the first side of the second bandage ply, which establish a detachable joining of first bandage ply and second bandage ply,
   wherein the three-dimensional structures on the surface of the first side of the second bandage ply comprise struts (14) present on or close to the surface of the first side of the second bandage ply, and also comprise cavities (13) open toward the surface, and , and wherein the cavities open towards the surface are cells which are present in the interior of the open-cell polymer foam and which are exposed and become the cavities open towards the surface by a cutting of the foam during the production of the second bandage ply and wherein the interior of the foam contains an intact cell structure which is not exposed by the cutting of the foam during the production of the second bandage ply
   wherein the three-dimensional structures on the surface of the second side of the first bandage ply are perforations (15) which are introduced into the film such that the perforation edges (16) protrude from solely the second surface of the film (11) to form crater-shaped structures on the second surface of the film (11), and the first surface of the first bandage ply is smooth, and
   wherein the crater-shaped structures present on the surface of the second side of the first bandage ply (11) can penetrate the cavities present on the surface of the second bandage ply (12) forming a form-fit and/or force-fit connection between the first bandage ply and the second bandage ply,
   such that the second bandage ply (12, 22), after application of the first ply to the wound base (3), can be joined to the first bandage ply (11, 21, 31), so as to prevent movement of the first bandage ply (11, 21, 31) with respect to the second bandage ply (12, 22) during the therapy and/or facilitating simultaneous removal of first (11, 21, 31) and second bandage ply (12, 22); and,
   iv) optionally, an airtight covering film (6) for closing the wound space.

7. The bandage set of claim 6 wherein the fluid-permeable open-cell polymer foam is a reticulated foam.

8. Product for use in therapeutic treatment of an open abdomen on a human or animal body by means of negative pressure, comprising
   a first bandage ply (11, 21, 31) having a first and a second side, as organ-protecting layer, the first side being intended for application to a wound base (3), wherein the first bandage ply comprises a fluid-permeable flexible film (11, 21, 31) composed of a polymeric material;
   a second bandage ply (12, 22) provided separately from the first bandage ply and having a first and a second side, the first side of the second bandage ply (12, 22) being intended for application to the second side of the first bandage ply (11, 21, 31), which second bandage ply (12, 22) does not come into direct contact with the wound base (3) wherein the second bandage ply comprises a fluid-permeable open-cell polymer foam (12, 22); and,
   three-dimensional structures (13, 14, 15, 16) on the surface of the second side of the first bandage ply (11) and the surface of the first side of the second bandage ply, which establish a detachable joining of first bandage ply and second bandage ply,
   wherein the three-dimensional structures on the surface of the first side of the second bandage ply comprise struts (14) present on or close to the surface of the first side of the second bandage ply, and also comprise cavities (13) open toward the surface, and wherein the cavities open towards the surface are cells which are present in the interior of the open-cell polymer foam and which are exposed and become the cavities open towards the surface by a cutting of the foam during the production of the second bandage ply and wherein the interior of the foam contains an intact cell structure which is not exposed by the cutting of the foam during the production of the second bandage ply and
   wherein the three-dimensional structures on the surface of the second side of the first bandage ply are perforations (15) which are introduced into the film such that the perforation edges (16) protrude solely from the second surface of the film (11) to form crater-shaped structures on the second surface of the film (11), and the first surface of the first bandage ply is smooth, and
   wherein the crater-shaped structures present on the surface of the second side of the first bandage ply (11) can penetrate the cavities present on the surface of the second bandage ply (12) forming a form-fit and/or force-fit connection between the first bandage ply and the second bandage ply, such that after application of the first ply to the wound base (3), the second bandage ply (12, 22) can be joined to the first bandage ply (11, 21, 31), so as to provide for the first bandage ply, during the therapy, to be held in an abdominal space at a position desired by the user by means of the second bandage ply (12, 22) and/or to facilitate safe removal of the first bandage ply (11, 21, 31) from the abdominal space after completion of the negative-pressure therapy by taking out the second bandage ply (12, 22).

9. The product of claim 8 wherein the wherein the fluid-permeable open-cell polymer foam is a reticulated foam.

10. An apparatus suitable for use in negative-pressure therapy of an open abdomen, consisting of:

a first bandage ply (11, 21, 31) having a first and a second side, the first side being, as organ-protecting layer, the first side being intended for application to a wound base (3) wherein the first bandage ply comprises a fluid-permeable flexible film (11, 21, 31) composed of a polymeric material; and, a second bandage ply (12, 22) provided separately from the first bandage ply and having a first and a second side, the first side of the second bandage ply (12, 22) being intended for application to the second side of the first bandage ply, which second bandage ply (12, 22) does not come into direct contact with the wound base (3) wherein the second bandage ply comprises a fluid-permeable open-cell polymer foam (12, 22); and, three-dimensional structures (13, 14, 15, 16) on the surface of the second side of the first bandage ply (11) and the surface of the first side of the second bandage ply, which establish a detachable joining of first bandage ply and second bandage ply, wherein the three-dimensional structures on the surface of the first side of the second bandage ply comprise struts (14) present on or close to the surface of the first side of the second bandage ply, and also comprise cavities (13) open toward the surface, and wherein the cavities open towards the surface are cells which are present in the interior of the open-cell polymer foam and which are exposed and become the cavities open towards the surface by a cutting of the foam during the production of the second bandage ply and wherein the interior of the foam contains an intact cell structure which is not exposed by the cutting of the foam during the production of the second bandage ply, and wherein the three-dimensional structures on the surface of the second side of the first bandage ply are perforations (15) which are introduced into the film such that the perforation edges (16) protrude from solely the second surface of the film (11) to form crater-shaped structures on the second surface of the film (11) and the first surface of the first bandage ply is smooth, and wherein the crater-shaped structures present on the surface of the second side of the first bandage ply (11) can penetrate the cavities present on the surface of the second bandage ply (12) forming a form-fit and/or force-fit connection between the first bandage ply and the second bandage ply, such that the second bandage ply (12, 22), after application of the first ply (11, 21, 31) to the wound base (3), can be joined to the first bandage ply (11, 21, 31), so as to prevent movement of the first bandage ply (11, 21, 31) with respect to the second bandage ply (12, 22) during the therapy and/or facilitates simultaneous removal of first (11, 21, 31) and second bandage ply (12, 22).

* * * * *